United States Patent
Lindholm-Ventola

[11] Patent Number: 5,695,446
[45] Date of Patent: Dec. 9, 1997

[54] APPARATUS TO BE USED IN COLLECTING SEMEN

[76] Inventor: Jukka Lindholm-Ventola, Mellıläntie 760, Fin-32200 Loimaa, Finland

[21] Appl. No.: 520,250

[22] Filed: Aug. 28, 1995

Related U.S. Application Data

[63] Continuation of Ser. No. 302,836, filed as PCT/FI93/00101, Mar. 19, 1993, abandoned.

[30] Foreign Application Priority Data

Mar. 19, 1992 [FI] Finland ................................ 921190

[51] Int. Cl.⁶ .................................................... A61F 5/00
[52] U.S. Cl. ................................................ 600/38; 604/349
[58] Field of Search ............................. 604/349, 350–53; 600/38–41

[56] References Cited

U.S. PATENT DOCUMENTS

| | | | |
|---|---|---|---|
| 4,312,350 | 1/1982 | Doan | 604/349 |
| 4,620,531 | 11/1986 | Dyer | 604/349 |
| 4,690,678 | 9/1987 | Douglas-Hamilton | 604/349 |
| 4,744,352 | 5/1988 | Emery | |

*Primary Examiner*—Lee S. Cohen
*Assistant Examiner*—Ryan Carter
*Attorney, Agent, or Firm*—Nixon & Vanderhye P.C.

[57] ABSTRACT

An artificial vagina for collecting semen used in animal breeding includes a heatable tubular jacket with a tubular interior component made of resilient material, surrounded by the jacket and fastened to it in a fluid-tight manner to define an annular chamber between the jacket and interior component. Heat is applied to the jacket, some of which is transferred to the interior component. Air is introduced into the annular chamber to establish an air layer, and the radial thickness of the air layer is steplessly adjusted (e.g. in a stimulation ring using different air connections) so that the rate of heat transfer between the jacket and interior component is controlled, and to facilitate use as an artificial vagina.

20 Claims, 5 Drawing Sheets

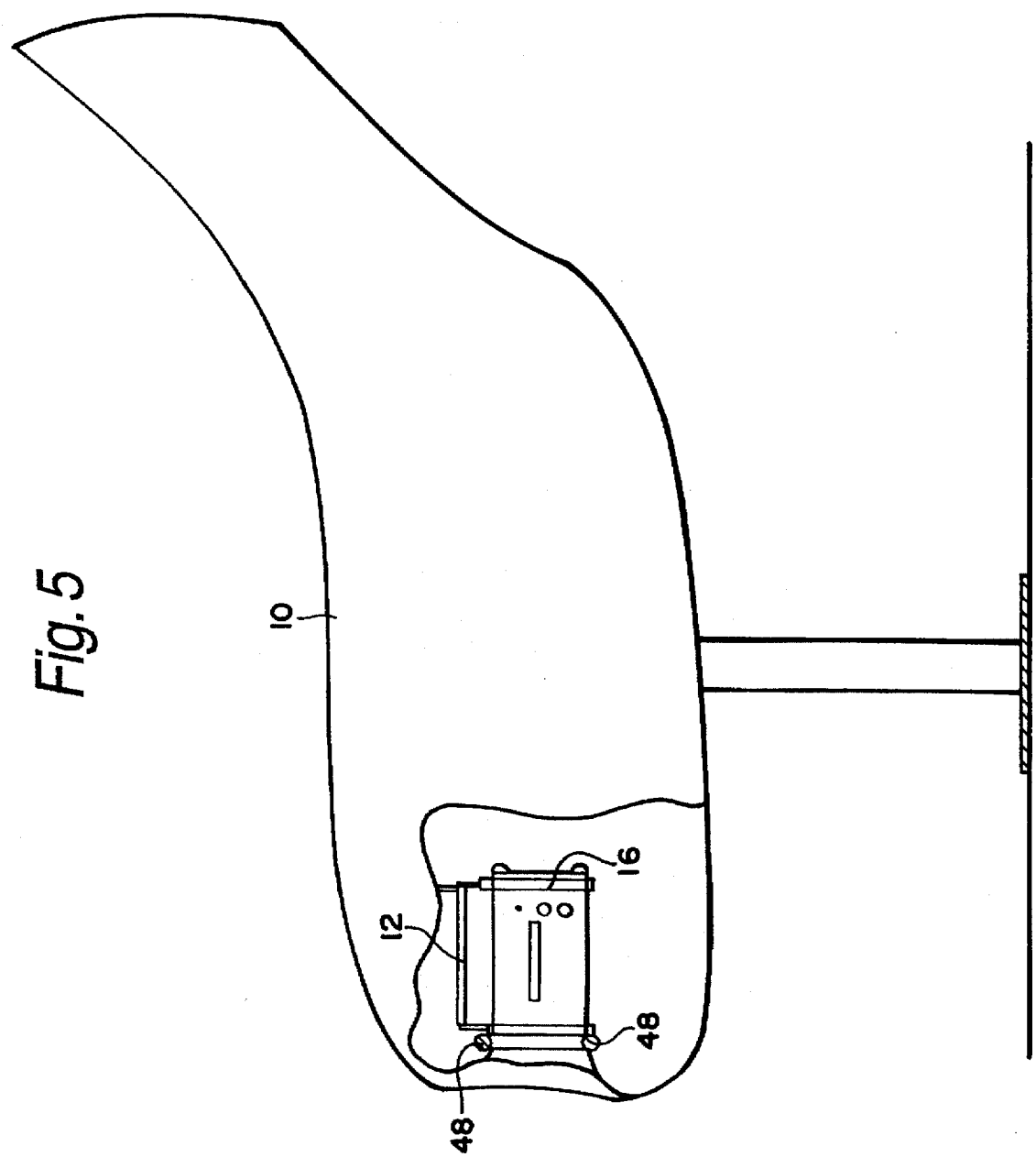

APPARATUS TO BE USED IN COLLECTING SEMEN

This is a continuation of application Ser. No. 08/302,836, filed as PCT/FI93/00101, Mar. 19, 1993, now abandoned.

OBJECT OF THE INVENTION

The object of the invention is an artificial vagina intended for collecting semen to be used in animal breeding, the apparatus comprising at least a tubular interior consisting of resilient rubber or equivalent material.

BACKGROUND OF THE INVENTION

Artificial insemination is used increasingly often in modern horse breeding. In Finland, for example, some 3500 mares were artificially inseminated in 1991. According to a known method, at artificial insemination centres, the semen of the stallion is usually collected by using an artificial vagina and dummy horse, or a mare in heat. To carry out the procedure, one person is required to hold the stallion and another to hold the mare, if there is no so-called breeding mount available. If an open artificial vagina is used, one person is also needed to collect the semen by means of a funnel.

The correct temperature of the artificial vaginas used as aids in collecting semen is of crucial importance when the stallion is serving. Presently, this is achieved by heating the vagina by pouring hot water (about 50°–57° C.) inside it. Air can also be added to the artificial vagina for tightening the vagina.

The disadvantage of the foregoing known method is that holding the artificial vagina is strenuous and dangerous, because when the stallion jumps on the breeding mount, it moves its legs vigorously, thus causing a dangerous situation for the persons holding the artificial vagina and funnel. One of the disadvantages of the presently used method is that the solidly fixed artificial vagina does not follow the movements of the stallion's penis unless the artificial vagina is held by hand. This is one of the reasons why some stallions do not ejaculate into an artificial vagina.

The inner diameter of presently used artificial vaginas can be changed in two ways. Either different sizes of vaginas are kept in store, or the amounts of air and water contained by the water-filled vagina are changed. In the first case, the method is inconvenient and expensive, because there must be several different sizes of vaginas and numerous different spare parts for them. With water-filled artificial vaginas, on the other hand, one would have to be familiar with the stallions to be able to anticipate the amount of warm water, because once serving has started, the size of the artificial vagina can no longer be changed. Adding water to the artificial vagina also tends to change the inner shape of the artificial vagina, because the mass of water pushes the vagina opening towards the lower edge of the vagina.

Another disadvantage of the devices used is that the temperature of the artificial vagina cannot be kept constant while collecting the semen. Should the stallion not ejaculate during the first or second jump, the temperature of the artificial vagina will fall, in which case the laborious process of changing the water inside the artificial vagina has to be carried out again, for the next attempt at collecting the semen. The size of presently used artificial vaginas cannot be changed very quickly either at the final stages of serving, except by opening the valve to allow water to flow out.

The aim of the present invention is to eliminate the foregoing problems and to achieve a new artificial vagina, by means of which the above disadvantages are eliminated.

SUMMARY OF THE INVENTION

It is characteristic of the invention that the artificial vagina comprises a heatable jacket tube, to the ends of which is fastened the tubular inner part coming inside it, and a connection for introducing air between the jacket tube and the interior part to form an air layer, and for adjusting the thickness of this air layer for heating and using the artificial vagina. It is also characteristic of the invention that there is a padded ring encircling the outward-directed end of the jacket tube, and at the other, inward-remaining end of the jacket tube, there is a hollow stimulation ring made of rubber or other resilient material inside the jacket tube, the amount of air in the interior air duct of the stimulation ring being adjustable through the connection, for heating and using the artificial vagina. The interior part passes around the padded ring and stimulation ring, over the ends of the jacket tube, for fastening.

By means of the invention, an underpressure is created in the air layer and air duct through the connections before serving takes place, so that the interior part presses at least for the most part against the interior surface of the jacket tube to heat the interior part quickly to the required temperature by means of the heating elements, and after this, air is supplied through the connections to the air layer and the air duct for adjusting the interior part and the size of the stimulation ring to suit each serving animal separately.

The temperature of the air layer and interior part is maintained correct by means of the heating elements at least for the duration of the possible preparation period, and towards the end or at the end of serving, the pressure in the air layer is lowered if necessary in order to facilitate the animal releasing itself from the artificial vagina.

By means of the apparatus, the movement of the artificial vagina resembles natural flexibility, and the safety of the assisting personnel and of the serving stallion are improved.

The artificial vagina is used either fastened to a dummy animal or breeding mount, or alternatively manually as a separate device.

The invention is described in the following with examples with reference to the appended drawings in which

BRIEF DESCRIPTION OF THE DRAWINGS

FIG. 5 shows the apparatus relating to the invention when placed in the dummy horse, as seen from the side and in partial cross section.

DESCRIPTION OF THE PREFERRED EMBODIMENTS

Figure 1:
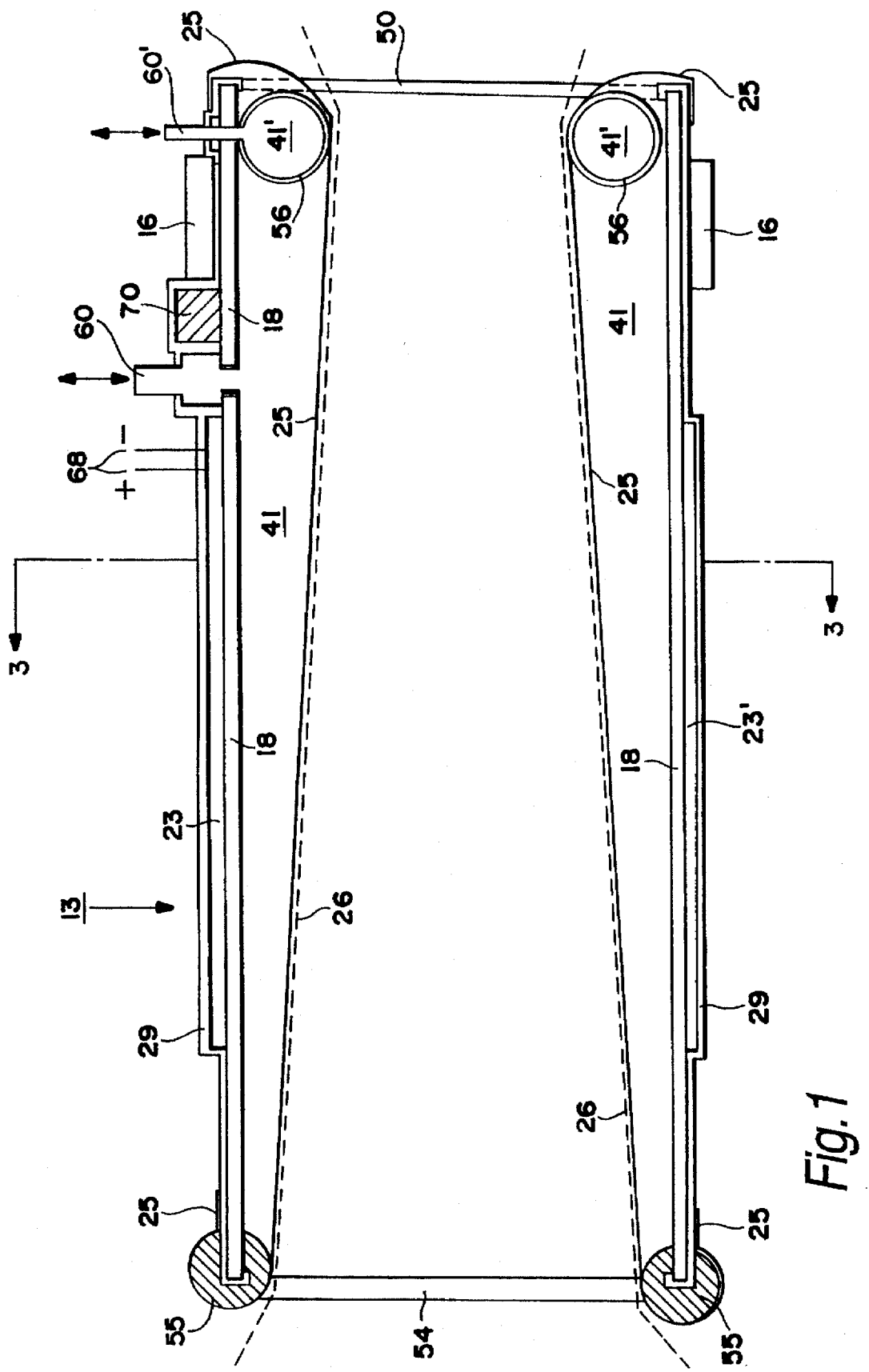
FIG. 1 shows the artificial vagina relating to the invention for facilitating the collection of the semen of a breeder.

FIG. 1 shows the artificial vagina 13 relating to the invention for facilitating the collection of the semen of a breeder. The main parts of the artificial vagina 13 are an aluminium jacket tube 18, and the heating elements 23 and 23' fastened on its outer surface. The other end of the jacket tube 18, the vagina opening 54 of the artificial vagina 13, is encircled by a padded ring 55 made from resilient material, and at the opposite end of the artificial vagina 13, to the rear part 50 of the artificial vagina on the interior surface of the jacket tube 18, is fastened a ring-like, air-filled stimulation ring 56 provided with an interior air duct 41'. The outer surface of the jacket tube 18 is covered with a tight rubber-like material 29 which repels humidity and dirt. The interior surface of the jacket tube 18 of the artificial vagina 13 is covered with a soft, resilient rubber film 25, which at the same time covers the padded ring 55 and the stimulation ring 56, and the end edges of which are turned over the jacket tube of the vagina 13. The rubber film 25 can be changed when necessary. Over the rubber film 25, through the artificial vagina 13, is in addition pulled a protective, disposable film 26 which is changed after each serving. Disposable protectors raise the level of hygiene and thus the risk of, for example, venereal disease infections between different stallions is avoided when using a common artificial vagina.

Compressed air is added between the jacket tube 18 and the rubber film 25 through a valve 60, thus making the resilience of the surface of the rubber film 25 steplessly adjustable and as soft as possible. Since the temperature of the interior surface of the artificial vagina 13 should correspond accurately to the temperature of a natural vagina, the air layer 41 inside the jacket tube 18 is heated by means of heating elements 23, 23' to exactly the desired temperature.

The shape of the interior surface of the artificial vagina 13 is changed by changing the pressure of the air layer 41 between the jacket tube 18 of the artificial vagina and the rubber film 25 through the valve 60. The size of the artificial vagina 13 should correspond as well as possible to that of the stallion's penis, and the size of the artificial vagina 13 can be steplessly adjusted also after serving has started, and during it. Thus the shape of the interior surface of the artificial vagina 13 remains as natural as possible, although its diameter changes.

The formed padding rubber covering the rear part of the interior surface of the jacket tube 18 of the artificial vagina 13, that is, the stimulation ring 56, has for its part a stimulating effect on the stallion's penis. The shape of the stimulation ring 56 is changed by changing the pressure of the air inside the ring in the air duct 41', by means of the valve 60'. By means of the stimulation ring 56, the obtaining of an erection in serving is significantly improved.

At the end of serving, the stallion often has difficulties in pulling its penis out of the artificial vagina 13, particularly if for some reason ejaculation does not take place, the penis thus remaining swollen and stiff. The size of the artificial vagina 13 can be adjusted so as to be larger when serving has ended, which is particularly important for the safety of the stallion. The size of the artificial vagina 13—the diameter of the interior surface—can be enlarged towards the end of serving by removing the air from between the jacket tube 18 and the rubber film 25, and from inside the stimulation ring 56. To the outer surface of the artificial vagina 13 is in addition fastened a support element 70 against which the locking bolt 16 holding the artificial vagina in place leans. All the functions of the artificial vagina 13 are monitored and controlled from a separate monitoring room located at a safe distance.

Figure 2:
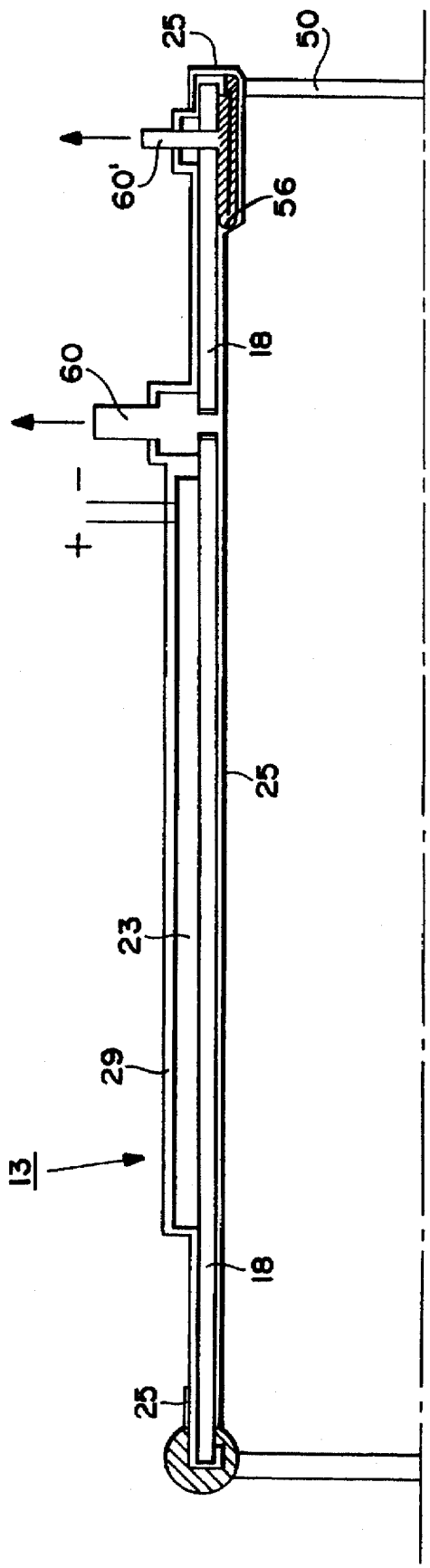
FIG. 2 shows the heating stage of the artificial vagina.

FIG. 2 shows the heating stage of the artificial vagina 13. When preparing the artificial vagina 13 for serving, the heating elements 23 on the outer surfaces of the jacket tube 18 heat the metal jacket 18. When the jacket 18 is heated, the heat released transfers to the air layer between the jacket 18 and the rubber film 25, and from there further to the rubber film 25. However, the temperature of the rubber film 25 of the artificial vagina 13 remains lower than that of the jacket tube 18, and it must be possible to raise the temperature of the rubber film 25 rapidly to serving temperature.

To eliminate the disadvantage, underpressure is utilized in heating the artificial vagina 13. The rubber film 25 is sucked by underpressure through the valve 60 into contact with the jacket tube 25, thus heating the film 25 rapidly to the correct temperature. At the same time, underpressure is sucked through the valve 60' into the air duct of the stimulation ring 56 covering the interior surface of the jacket tube 18 of the artificial vagina 13, and the transfer of heat over the entire interior surface of the artificial vagina 13 is thus made more efficient. As serving starts, the underpressure is changed to a preset overpressure, thus adjusting the size of the artificial vagina 13 automatically to the right size.

Correspondingly, at the end of the serving by the stallion, the overpressure in the artificial vagina 13 is changed to underpressure, and the rubber film 25 and stimulation ring 56 are again sucked into contact with the jacket tube 18. By alternating over- and underpressure, the inner diameter of the artificial vagina 13 can be changed throughout serving.

Figure 3:
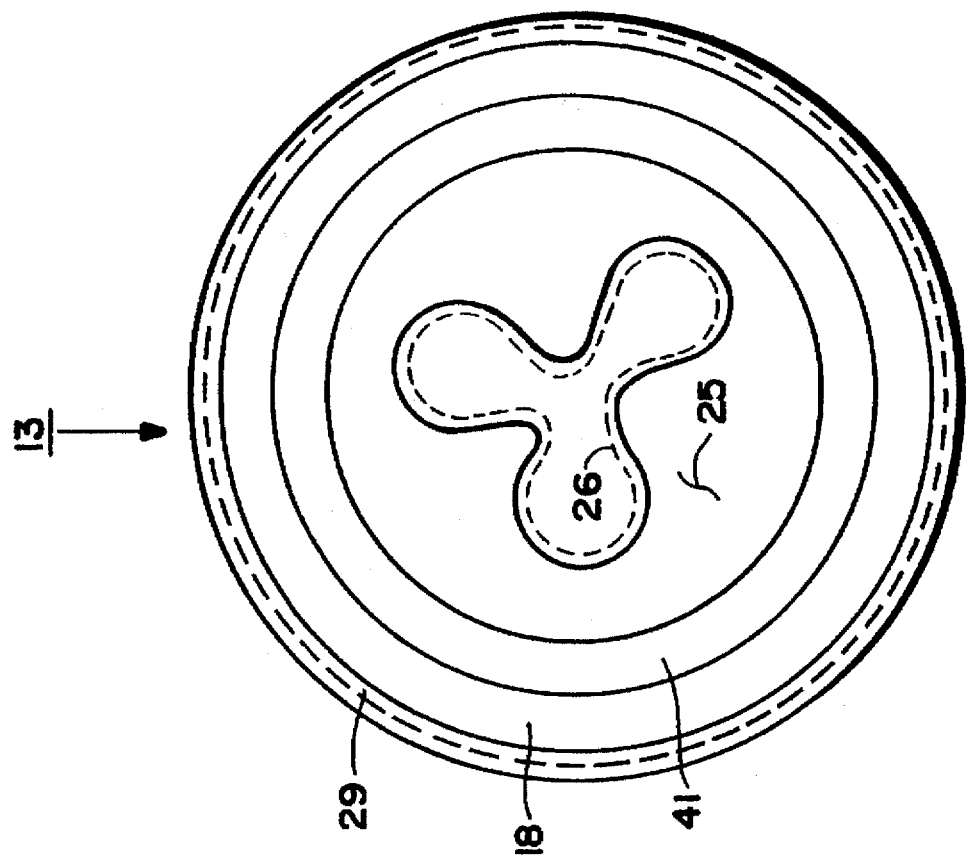
FIG. 3 shows the section III—III of FIG. 1.

FIG. 3 shows the sectional view III—III of FIG. 1. The main parts of the artificial vagina 13 are the aluminium jacket tube 18, and the heating elements fastened on its outer surface. The outer surface of the jacket tube 18 is covered with a tight rubber-like material 29 which repels humidity and dirt. The interior surface of the jacket tube 18 of the artificial vagina 13 is covered with a soft, resilient rubber film 25, which an the same time covers the padded ring and the stimulation ring, and the end edges of which are turned over the artificial vagina 13. Between the jacket tube 18 and the rubber film 25 is formed an air layer 41, which makes the resilience of the surface of the rubber film 25 steplessly adjustable and as soft as possible. When the shape of the interior surface of the artificial vagina 13 is changed, the pressure of the air layer 41 between the jacket tube 18 and rubber film 25 is changed. The shape of the interior surface of the artificial vagina 13 should correspond as closely as possible to the size of the stallion's penis, and the size of the artificial vagina 13 can be changed steplessly, also once serving has started, and during it. Thus the shape of the vagina 13 remains as natural as possible, although its diameter changes. Over the rubber film 25, through the artificial vagina 13 is pulled a protective disposable film 26, which is changed after each serving.

Figure 4:
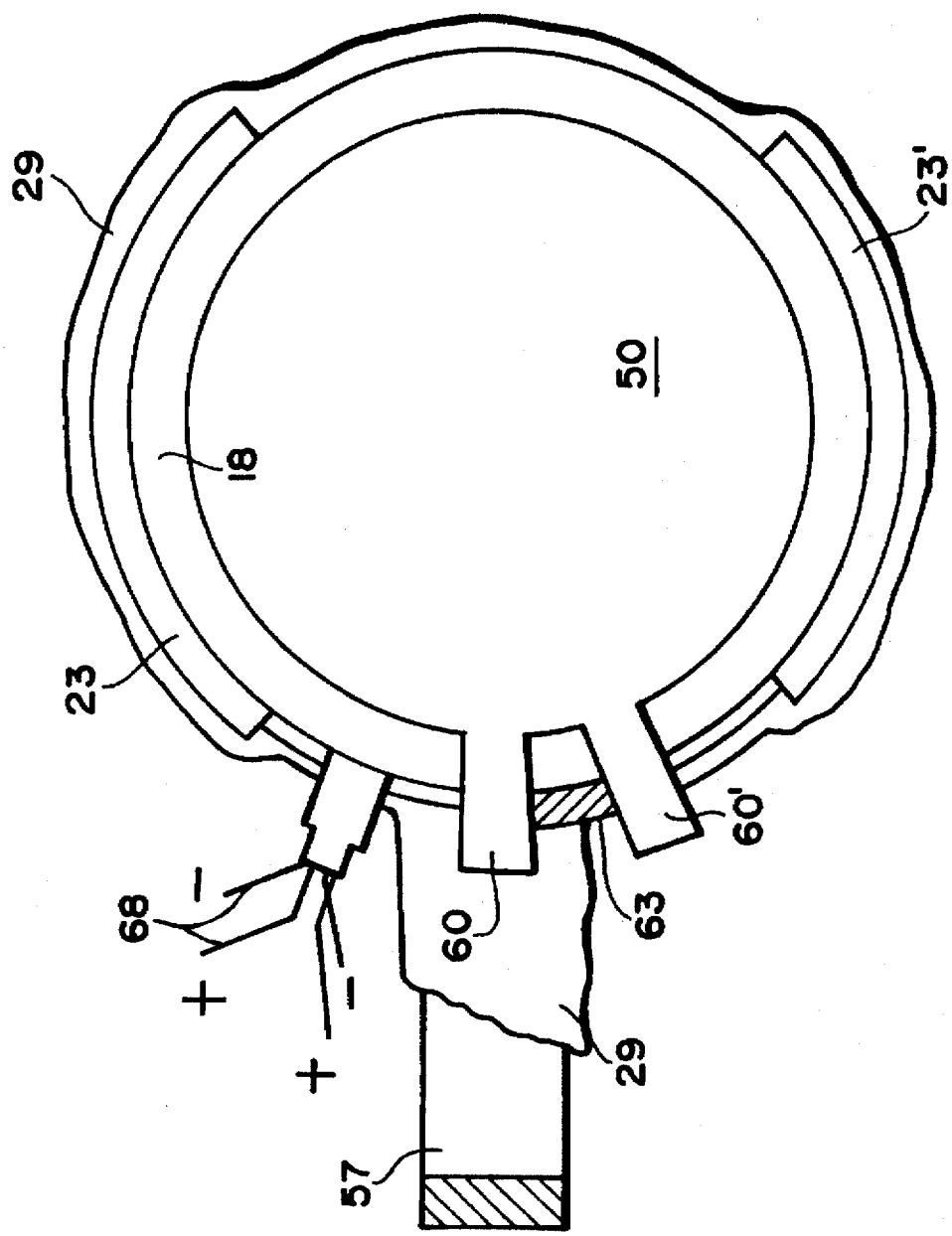
FIG. 4 shows the structure of the jacket tube of the artificial vagina as seen from the front and in partial cross section.

FIG. 4 shows the structure of the jacket tube 18 of the artificial vagina 13 as seen from the front and in partial cross section. The main parts of the artificial vagina 13 are the aluminium jacket tube 18, and the heating resistors 23, 23' fastened on its outer surface. The outer surface of the jacket tube 18 is covered with a tight rubber-like material 29 which repels humidity and dirt. The rubber layer 29 also covers the lifting handle 57, which facilitates the handling and transportation of the artificial vagina. In the jacket tube 18 connections have been made for the valves 60, 60', by means of which the over- or underpressure maintained in the artificial vagina is adjusted. The operation of the heating elements 23, 23' is controlled through the connection 68. The jacket tube 18 also comprises a temperature measuring sensor 63 for adjusting the temperature of the heating elements to the desired value.

FIG. 5 shows the artificial vagina relating to the invention when placed in the dummy horse, as seen from the side and in partial cross section. Inside the rear part of the frame 10 of the dummy horse covered with resilient material is installed a frame 12 for the artificial vagina. The artificial vagina 13 is placed in the frame 12 by pushing the artificial vagina 13 into the opening encircled by the holder 48 in the rear part of the frame, and by locking from the front by means of the locking bolt 16.

The whole artificial vagina 13 is removed for servicing, cleaning, or use independent of the dummy horse by opening the locking bolt 16 and remove the artificial vagina from the dummy horse from below. For use independent of the dummy horse, the artificial vagina 13 is prepared through the heating and pressure-balancing stages in the dummy horse, from which it is then removed and taken to the place of use.

It is obvious to a person skilled in the art that the different embodiments of the invention may vary within the claims presented.

I claim:

1. An artificial vagina for collecting semen, comprising:
   a heatable tubular jacket having first and second ends;
   a tubular interior component made of resilient material and disposed within said jacket, and radially surrounded by said jacket and fastened in a substantially fluid-tight manner to said jacket adjacent said jacket first and second ends, with a substantially annular chamber defined between said jacket and said interior component, said annular chamber having an air layer of variable radial thickness therein;
   a first connection for introducing an amount of air into said substantially annular chamber; and
   wherein there is a rate of heat transfer between said jacket and said interior component: and
   means for steplessly adjusting the radial thickness of said air layer between said jacket and said interior component so that the rate of heat transfer between said jacket and said interior component is controlled.

2. An artificial vagina as recited in claim 1 further comprising a padded ring at said jacket first end, said interior component extending over said padded ring.

3. An artificial vagina as recited in claim 2 further comprising a hollow stimulation ring of resilient material disposed within said jacket adjacent said second end thereof and having an interior volume, said interior component extending over said stimulation ring; a second connection for introducing air into said stimulation ring; and wherein said means for steplessly adjusting the thickness of said air layer includes means for steplessly adjusting the amount of air in said stimulation ring to thereby increase or decrease the interior volume of said stimulation ring.

4. An artificial vagina as recited in claim 3 wherein said jacket comprises a metal tube having an outer surface; and further comprising at least one electric heating element mounted to said metal tube outer surface for heating said jacket and said air layer.

5. An artificial vagina as recited in claim 4 wherein said means for steplessly adjusting the thickness of said air layer between said jacket and said interior component comprises a duct, air pump, and valve.

6. An artificial vagina as recited in claim 4 wherein said means for steplessly adjusting the thickness of said air layer between said jacket and said interior component comprises a separate source of air connected to each of said first and second connections to provide for separately controlled introduction, or removal, of air through each of said connections.

7. An artificial vagina as recited in claim 5 further comprising a temperature sensor mounted in association with said jacket, said sensor connected to said at least one heating element to effect control thereof.

8. An artificial vagina as recited in claim 1 disposed within a dummy animal body having an exterior, with said first end of said tubular interior component open, and open to the exterior of said dummy animal.

9. An artificial vagina as recited in claim 3 disposed within a dummy animal body having an exterior, with said first end of said tubular interior component open, and open to the exterior of said dummy animal.

10. An artificial vagina as recited in claim 4 disposed within a dummy animal body having an exterior, with said first end of said tubular interior component open, and open to the exterior of said dummy animal.

11. An artificial vagina as recited in claim 1 wherein said jacket comprises a metal tube having an outer surface; and further comprising at least one electric heating element mounted to said metal tube outer surface for heating said jacket and said air layer.

12. An artificial vagina as recited in claim 1 wherein said means for steplessly adjusting the thickness of said air layer between said jacket and said interior component comprises a duct, air pump, and valve.

13. An artificial vagina as recited in claim 11 further comprising a temperature sensor mounted in association with said jacket, said sensor connected to said at least one heating element to effect control thereof.

14. An artificial vagina as recited in claim 3 wherein said tubular interior component and said hollow stimulation ring are both made of rubber.

15. A method for collecting semen for use in animal breeding using an artificial vagina comprising: a heatable tubular jacket having first and second ends; a tubular interior component made of resilient material and disposed within the jacket, and fastened in a substantially fluid-tight manner to the jacket adjacent the jacket first and second ends, with a substantially annular chamber defined between the jacket and the interior component, the annular chamber having an air layer of variable thickness therein; and a first connection for introducing air into the substantially annular chamber; said method comprising the steps of:
   (a) controlling the thickness of the air layer in the substantially annular chamber so that an under-pressure of sufficient magnitude is created to cause the majority of the resilient material tubular interior component to come into contact with the jacket to effect rapid heat transfer between the jacket and the interior component;
   (b) supplying heat to the jacket, some of which is transferred to the interior component; and
   (c) after the interior component has reached a desired temperature, steplessly controlling the thickness of air in the annular chamber so as to provide a desired air layer thickness for the artificial vagina to facilitate collection of semen from a breeding animal.

16. A method as recited in claim 15 wherein steps (a) and (c) are practiced by withdrawing air from, and introducing air into, the air layer through the first connection.

17. A method as recited in claim 15 comprising the further step of, after step (c) is practiced to either collect semen, or when an attempt to collect semen is unsuccessful, reducing the air layer thickness so that easy withdrawal of the penis of a breeding animal is provided.

18. A method as recited in claim 15 further comprising a hollow stimulation ring of resilient material disposed within the jacket adjacent the second end thereof, the interior component extending over the stimulation ring, and a second connection for introducing air into the stimulation ring; and wherein said method comprises the further step (d) of steplessly adjusting the amount of air in the stimulation ring to thereby increase or decrease the interior volume of the stimulation ring.

19. A method as recited in claim 16 further comprising a hollow stimulation ring of resilient material disposed within the jacket adjacent the second end thereof, the interior component extending over the stimulation ring, and a second connection for introducing air into the stimulation ring; and wherein said method comprises the further step (d) of steplessly adjusting the amount of air in the stimulation ring to thereby increase or decrease the interior volume of the stimulation ring.

20. A method as recited in claim 15 comprising the further steps of placing a clean protective film on the interior of the tubular interior component, using the artificial vagina to collect semen from a breeding animal, and then replacing the film with another clean protective film.

* * * * *